United States Patent [19]

Schumann

[11] Patent Number: Plant 5,932

[45] Date of Patent: Apr. 7, 1987

[54] GERANIUM PLANT NAMED COLUMBIA

[75] Inventor: Ingeborg Schumann, Bad Ems, Fed. Rep. of Germany

[73] Assignee: Fischer Geraniums, Inc., Netherlands Antilles

[21] Appl. No.: 761,012

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Columbia having red flowering startel flower type with strong divided petals; novel, decorative zonal foliage; compact growth habit with good branching; and heavy flower yield.

2 Drawing Figures

1

The present invention comprises a new and distinct cultivar of geranium, botanically known as *Pelargonium zonale,* and hereinafter referred to by the cultivar name Columbia.

Columbia is a product of a planned breeding program which had the objective of creating new geranium cultivars having novel flower startel type and unique leaf shape.

Columbia was originated from a hybridization made by Ingeborg Schumann in a controlled breeding program in Hillscheid, Federal Republic of Germany in 1978. The female parent was an inbred line from H43 and Stellar Artic Star. The male parent of Columbia was Stellar Orange. Both parents are unpatented.

Columbia was discovered and selected as one flowering plant within the progeny of the stated cross by Ingeborg Schumann on June 13, 1979 in a controlled environment in Hillscheid, Federal Republic of Germany.

The first act of asexual reproduction of Columbia was accomplished when vegetative cuttings were taken from the initial selection in January of 1980 in a controlled environment in Hillscheid, Federal Republic of Germany by a technician working under formulations established and supervised by Ingeborg Schumann. Horticultural examination of selected units initiated in the spring of 1980 and continued in 1981 through 1983 has demonstrated that the combination of characteristics as herein disclosed for Columbia are firmly fixed and are retained through successive generations of asexual reproduction.

Columbia has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Columbia, which in combination distinguish this geranium as a new and distinct cultivar.

1. Red flowers with startel flower type; divided petals are strong.
2. Novel leaf shape; generally star shaped; very decorative.
3. Compact habit with good branching.

2

4. Early response and heavy flower yield in spring and summer.

The accompanying photographic drawings shows typical flower and foliage characteristics of Columbia, with colors being as true as possible with illustrations of this type.

Sheet 1 is a color photograph showing Columbia in perspective view.

Sheet 2 is a black and white print showing the novel leaf shape of Columbia, at three stages of growth.

In the following description color references are made to The Royal Horticultural Society Colour Chart. The color values are determined between 2:00 p.m. and 3:00 p.m. on May 15, 1985 under 20,000 Lux light intensity at Hillscheid, Federal Republic of Germany.

Classification:

*Botanical.*—A hybrid of the genus *Pelargonium l'hert* and species *Pelargonium zonale.*

*Commercial.*—Columbia.

INFLORESCENCE

A. Umbel:
- *Average diameter.*—81 mm.
- *Average depth.*—46 mm.
- *Peduncle length.*—138 mm.
- *Pedicel length.*—24 mm.

B. Corolla:
- *Average diameter.*—38 mm.
- *Form.*—Single flower; petals have relatively sharp tips.
- *Color (general tonality from a distance of three meters).*—Red. Upper surface: 44B.

C. Bud:
- *Shape.*—Elongated, flat top.
- *Color.*—Red, partly marbled.

D. Reproductive organs:
- *Androecium.*—Mostly sterile; sometimes 6–7 anthers.
- *Gynoecium.*—4–5 lobed stigma.

E. Spring flowering response period: In Hillscheid, Federal Republic of Germany, in 1983, 90% of plants opened with at least one flower 13 weeks after planting of unrooted cuttings.

F. Outdoor flower production: The total flower count in 1983 in Hillscheid, Federal Republic of Germany, was between 67 and 70 flowers per plant for the June through October observation period.

G. Durability: Good.

PLANT

A. Foliage:

*Form.*—Generally star shaped; novel.

*Margin.*—Deeply indented, forming separate leaf segments; leaf tips relatively pointed.

*Color.*—Top surface: Medium green, approximately 137B-C. Zonation: Generally brown, medium zonation, primarily at margin of leaves.

*Tolerance of botrytis.*—Good.

B. General appearance and form:

*Internode length.*—17 mm.

*Branching pattern.*—4.5 branches within a period of 13 weeks cultivation from unrooted cuttings.

*Height.*—260 mm.

I claim:

1. A new and distinct cultivar of geranium named Columbia, as described and illustrated, and particularly characterized by its red flowering startel flower type, with strong divided petals; novel, decorative zonal foliage; compact growth habit with good branching; and its heavy flower yield.

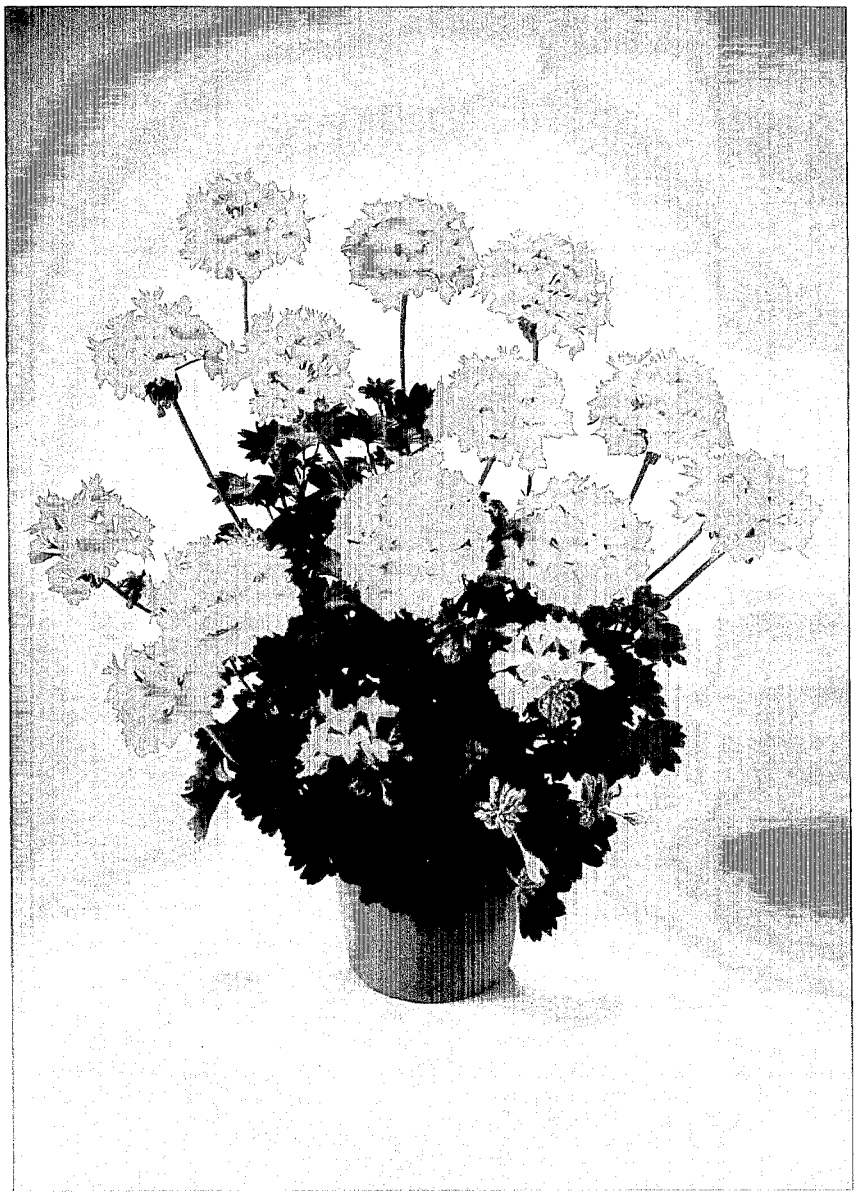

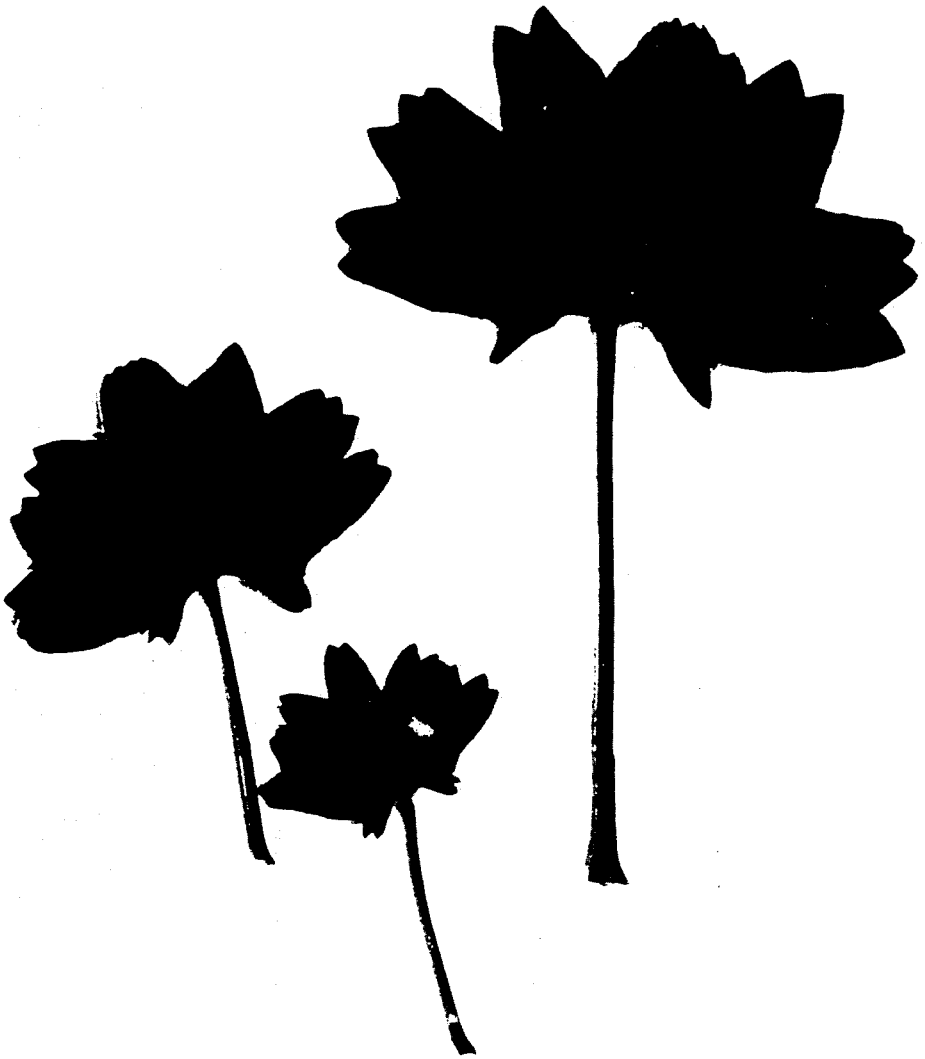

* * * * *